(12) United States Patent
Patel et al.

(10) Patent No.: US 8,361,097 B2
(45) Date of Patent: Jan. 29, 2013

(54) CATHETER SYSTEM AND METHOD FOR BORING THROUGH BLOCKED VASCULAR PASSAGES

(75) Inventors: Himanshu N. Patel, San Jose, CA (US); John B. Simpson, Woodside, CA (US)

(73) Assignee: Avinger, Inc., Redwood City, CA (US)

( * ) Notice: Subject to any disclaimer, the term of this patent is extended or adjusted under 35 U.S.C. 154(b) by 0 days.

(21) Appl. No.: 13/277,167

(22) Filed: Oct. 19, 2011

(65) Prior Publication Data

US 2012/0041307 A1 Feb. 16, 2012
US 2012/0209112 A2 Aug. 16, 2012

Related U.S. Application Data

(63) Continuation of application No. 12/108,433, filed on Apr. 23, 2008, now Pat. No. 8,062,316.

(51) Int. Cl.
*A61B 17/22* (2006.01)
*A61D 1/02* (2006.01)

(52) U.S. Cl. ........... 606/159; 606/171; 606/185; 606/80

(58) Field of Classification Search .................. 606/159, 606/194, 180, 80, 185, 171, 170; 30/29.5, 30/143, 151; 604/22, 164.01
See application file for complete search history.

(56) References Cited

U.S. PATENT DOCUMENTS

| 4,178,935 | A | 12/1979 | Gekhaman et al. |
| 4,552,554 | A | 11/1985 | Gould et al. |
| 4,654,024 | A | 3/1987 | Crittenden et al. |
| 4,686,982 | A | 8/1987 | Nash |
| 4,771,774 | A | 9/1988 | Simpson et al. |
| 5,047,040 | A | 9/1991 | Simpson et al. |
| 5,085,662 | A | 2/1992 | Willard |
| 5,182,291 | A | 1/1993 | Gubin et al. |
| 5,190,050 | A | 3/1993 | Nitzsche |
| 5,312,415 | A | 5/1994 | Palermo |
| 5,312,425 | A | 5/1994 | Evans et al. |
| 5,321,501 | A | 6/1994 | Swanson et al. |
| 5,358,472 | A | 10/1994 | Vance et al. |

(Continued)

FOREIGN PATENT DOCUMENTS

| EP | 1859732 A1 | 11/2007 |
| KR | 2007/0047221 | 5/2007 |

(Continued)

OTHER PUBLICATIONS

Sharma et al.; Optical coherence tomography based on an all-fiber autocorrelator using probe-end reflection as reference; CWJ13; San Francisco, California; CLEO May 16, 2004; 4 pages.

(Continued)

*Primary Examiner* — Ryan Severson
*Assistant Examiner* — Tin Nguyen
(74) *Attorney, Agent, or Firm* — Shay Glenn LLP

(57) ABSTRACT

A rotating cutting head catheter for passage through chronic total occlusions or other refractory atherosclerotic plaque from diseased arteries is disclosed. The catheter's rotating cutting head is designed to reside safely within an outer protective sheath when not in use. The outer protective sheath contains one or more helical grooves or slots, and the cutting head contains protruding blades or projections that fit into these helical grooves or slots. Application of torque to an inner catheter or wire attached to the cutting head applies spin to the cutting head, and the force of the sheath's helical grooves or slots against the cutting head's protruding blades or projections advances the cutting head outward from the protective sheath. Once extended, the cutting head may now rotate freely. The device may use a guidewire to direct the cutting head to the desired position.

17 Claims, 6 Drawing Sheets

U.S. PATENT DOCUMENTS

| | | |
|---|---|---|
| 5,383,467 A | 1/1995 | Auer et al. |
| 5,459,570 A | 10/1995 | Swanson et al. |
| 5,465,147 A | 11/1995 | Swanson |
| 5,556,405 A | 9/1996 | Lary |
| 5,632,754 A | 5/1997 | Farley et al. |
| 5,674,232 A | 10/1997 | Halliburton |
| 5,681,336 A | 10/1997 | Clement et al. |
| 5,690,634 A | 11/1997 | Muller et al. |
| 5,722,403 A | 3/1998 | McGee et al. |
| 5,795,295 A | 8/1998 | Hellmuth et al. |
| 5,830,145 A | 11/1998 | Tenhoff |
| 5,843,050 A | 12/1998 | Jones et al. |
| 5,868,778 A | 2/1999 | Gershony et al. |
| 5,872,879 A | 2/1999 | Hamm |
| 5,904,651 A | 5/1999 | Swanson et al. |
| 5,938,602 A | 8/1999 | Lloyd |
| 5,951,482 A | 9/1999 | Winston et al. |
| 5,951,581 A | 9/1999 | Saadat et al. |
| 5,951,583 A | 9/1999 | Jensen et al. |
| 5,956,355 A | 9/1999 | Swanson et al. |
| 5,957,952 A | 9/1999 | Gershony et al. |
| 6,001,112 A | 12/1999 | Taylor |
| 6,007,530 A | 12/1999 | Dornhofer et al. |
| 6,010,449 A | 1/2000 | Selmon et al. |
| 6,013,072 A | 1/2000 | Winston et al. |
| 6,017,359 A | 1/2000 | Gershony et al. |
| 6,027,514 A | 2/2000 | Stine et al. |
| 6,048,349 A | 4/2000 | Winston et al. |
| 6,080,170 A | 6/2000 | Nash et al. |
| 6,106,515 A | 8/2000 | Winston et al. |
| 6,110,164 A | 8/2000 | Vidlund |
| 6,120,515 A | 9/2000 | Rogers et al. |
| 6,120,516 A | 9/2000 | Selmon et al. |
| 6,134,002 A | 10/2000 | Stimson et al. |
| 6,134,003 A | 10/2000 | Tearney et al. |
| 6,152,938 A | 11/2000 | Curry |
| 6,152,951 A | 11/2000 | Hashimoto et al. |
| 6,160,826 A | 12/2000 | Swanson et al. |
| 6,175,669 B1 | 1/2001 | Colston et al. |
| 6,193,676 B1 | 2/2001 | Winston et al. |
| 6,206,898 B1 | 3/2001 | Honeycutt et al. |
| 6,228,076 B1 | 5/2001 | Winston et al. |
| 6,241,744 B1 | 6/2001 | Imran et al. |
| 6,283,957 B1 | 9/2001 | Hashimoto et al. |
| 6,290,668 B1 | 9/2001 | Gregory et al. |
| 6,294,775 B1 | 9/2001 | Seibel et al. |
| 6,299,622 B1 | 10/2001 | Snow et al. |
| 6,307,985 B1 | 10/2001 | Murakami et al. |
| 6,445,939 B1 | 9/2002 | Swanson et al. |
| 6,447,525 B2 | 9/2002 | Follmer et al. |
| 6,451,036 B1 | 9/2002 | Heitzmann et al. |
| 6,454,779 B1 | 9/2002 | Taylor |
| 6,482,217 B1 | 11/2002 | Pintor et al. |
| 6,485,413 B1 | 11/2002 | Boppart et al. |
| 6,497,649 B2 | 12/2002 | Parker et al. |
| 6,501,551 B1 | 12/2002 | Tearney et al. |
| 6,503,261 B1 | 1/2003 | Bruneau et al. |
| 6,563,105 B2 | 5/2003 | Seibel et al. |
| 6,564,087 B1 | 5/2003 | Pitris et al. |
| 6,565,588 B1 | 5/2003 | Clement et al. |
| 6,579,298 B1 | 6/2003 | Bruneau et al. |
| 6,638,233 B2 | 10/2003 | Corvi et al. |
| 6,666,874 B2 | 12/2003 | Heitzmann et al. |
| 6,687,010 B1 | 2/2004 | Horii |
| 6,728,571 B1 | 4/2004 | Barbato |
| D489,973 S | 5/2004 | Root et al. |
| 6,730,063 B2 | 5/2004 | Delaney et al. |
| 6,800,085 B2 | 10/2004 | Selmon et al. |
| 6,818,001 B2 | 11/2004 | Wulfman et al. |
| 6,830,577 B2 | 12/2004 | Nash et al. |
| 6,845,190 B1 | 1/2005 | Smithwick et al. |
| 6,852,109 B2 | 2/2005 | Winston et al. |
| 6,853,457 B2 | 2/2005 | Bjarklev et al. |
| 6,856,712 B2 | 2/2005 | Fauver et al. |
| 6,867,753 B2 | 3/2005 | Chinthammit et al. |
| 6,879,851 B2 | 4/2005 | McNamara et al. |
| 6,947,787 B2 | 9/2005 | Webler |
| 6,961,123 B1 | 11/2005 | Wang et al. |
| 6,970,732 B2 | 11/2005 | Winston et al. |
| 6,975,898 B2 | 12/2005 | Seibel |
| 7,068,878 B2 | 6/2006 | Crossman-Bosworth et al. |
| 7,074,231 B2 | 7/2006 | Jang |
| 7,126,693 B2 | 10/2006 | Everett et al. |
| 7,172,610 B2 | 2/2007 | Heitzmann et al. |
| 7,235,088 B2 | 6/2007 | Pintor et al. |
| 7,242,480 B2 | 7/2007 | Alphonse |
| 7,261,687 B2 | 8/2007 | Yang |
| 7,288,087 B2 | 10/2007 | Winston et al. |
| 7,291,146 B2 | 11/2007 | Steinke et al. |
| 7,297,131 B2 | 11/2007 | Nita |
| 7,311,723 B2 | 12/2007 | Seibel et al. |
| 7,344,546 B2 | 3/2008 | Wulfman et al. |
| 7,366,376 B2 | 4/2008 | Shishkov et al. |
| 7,382,949 B2 | 6/2008 | Bouma et al. |
| 7,426,036 B2 | 9/2008 | Feldchtein et al. |
| 7,428,001 B2 | 9/2008 | Schowengerdt et al. |
| 7,428,053 B2 | 9/2008 | Feldchtein et al. |
| 7,455,649 B2 | 11/2008 | Root et al. |
| 7,474,407 B2 | 1/2009 | Gutin |
| 7,485,127 B2 | 2/2009 | Nistal |
| 7,488,340 B2 | 2/2009 | Kauphusman et al. |
| 7,530,948 B2 | 5/2009 | Seibel et al. |
| 7,530,976 B2 | 5/2009 | MacMahon et al. |
| 7,538,859 B2 | 5/2009 | Tearney et al. |
| 7,538,886 B2 | 5/2009 | Feldchtein |
| 7,539,362 B2 | 5/2009 | Teramura |
| 7,542,145 B2 | 6/2009 | Toida et al. |
| 7,544,162 B2 | 6/2009 | Ohkubo |
| 7,545,504 B2 | 6/2009 | Buckland et al. |
| 7,555,333 B2 | 6/2009 | Wang et al. |
| 7,577,471 B2 | 8/2009 | Camus et al. |
| 7,583,872 B2 | 9/2009 | Seibel et al. |
| 7,616,986 B2 | 11/2009 | Seibel et al. |
| 7,674,253 B2 | 3/2010 | Fisher et al. |
| 7,706,863 B2 | 4/2010 | Imanishi et al. |
| 7,728,985 B2 | 6/2010 | Feldchtein et al. |
| 7,734,332 B2 | 6/2010 | Sher |
| 7,738,945 B2 | 6/2010 | Fauver et al. |
| 7,785,286 B2 | 8/2010 | Magnin et al. |
| 7,813,609 B2 | 10/2010 | Petersen et al. |
| 7,821,643 B2 | 10/2010 | Amazeen et al. |
| 8,062,316 B2 | 11/2011 | Patel et al. |
| 2001/0004700 A1 | 6/2001 | Honeycutt et al. |
| 2001/0020126 A1 | 9/2001 | Swanson et al. |
| 2002/0019644 A1 | 2/2002 | Hastings et al. |
| 2002/0077642 A1 | 6/2002 | Patel et al. |
| 2002/0082626 A1 | 6/2002 | Donohoe et al. |
| 2002/0111548 A1 | 8/2002 | Swanson et al. |
| 2003/0045835 A1 | 3/2003 | Anderson et al. |
| 2003/0097044 A1 | 5/2003 | Rovegno |
| 2003/0120295 A1 | 6/2003 | Simpson et al. |
| 2003/0125757 A1 | 7/2003 | Patel et al. |
| 2003/0125758 A1 | 7/2003 | Simpson et al. |
| 2004/0082850 A1 | 4/2004 | Bonner et al. |
| 2004/0147934 A1 | 7/2004 | Kiester |
| 2004/0167553 A1 | 8/2004 | Simpson et al. |
| 2004/0167554 A1 | 8/2004 | Simpson et al. |
| 2004/0181249 A1 | 9/2004 | Torrance et al. |
| 2004/0220519 A1 | 11/2004 | Wulfman et al. |
| 2004/0230212 A1 | 11/2004 | Wulfman |
| 2004/0230213 A1 | 11/2004 | Wulfman et al. |
| 2004/0236312 A1 | 11/2004 | Nistal et al. |
| 2004/0243162 A1 | 12/2004 | Wulfman et al. |
| 2004/0254599 A1 | 12/2004 | Lipoma et al. |
| 2005/0020925 A1 | 1/2005 | Kleen et al. |
| 2005/0043614 A1 | 2/2005 | Huizenga et al. |
| 2005/0054947 A1 | 3/2005 | Goldenberg |
| 2005/0085708 A1 | 4/2005 | Fauver et al. |
| 2005/0085721 A1 | 4/2005 | Fauver et al. |
| 2005/0154407 A1 | 7/2005 | Simpson |
| 2005/0159731 A1 | 7/2005 | Lee |
| 2005/0177068 A1 | 8/2005 | Simpson |
| 2005/0182295 A1 | 8/2005 | Soper et al. |
| 2005/0187571 A1 | 8/2005 | Maschke |
| 2005/0192496 A1 | 9/2005 | Maschke |
| 2005/0222519 A1 | 10/2005 | Simpson |
| 2005/0222663 A1 | 10/2005 | Simpson et al. |

| | | |
|---|---|---|
| 2005/0251116 A1 | 11/2005 | Steinke et al. |
| 2006/0032508 A1 | 2/2006 | Simpson |
| 2006/0064009 A1 | 3/2006 | Webler et al. |
| 2006/0109478 A1 | 5/2006 | Tearney et al. |
| 2006/0135870 A1 | 6/2006 | Webler |
| 2006/0229646 A1 | 10/2006 | Sparks |
| 2006/0229659 A1 | 10/2006 | Gifford et al. |
| 2006/0235366 A1 | 10/2006 | Simpson |
| 2006/0236019 A1 | 10/2006 | Soito et al. |
| 2006/0239982 A1 | 10/2006 | Simpson |
| 2006/0241503 A1 | 10/2006 | Schmitt et al. |
| 2006/0252993 A1 | 11/2006 | Freed et al. |
| 2006/0264741 A1 | 11/2006 | Prince |
| 2007/0010840 A1 | 1/2007 | Rosenthal et al. |
| 2007/0015979 A1 | 1/2007 | Redel |
| 2007/0038061 A1 | 2/2007 | Huennekens et al. |
| 2007/0038173 A1 | 2/2007 | Simpson |
| 2007/0078469 A1 | 4/2007 | Soito et al. |
| 2007/0196926 A1 | 8/2007 | Soito et al. |
| 2007/0276419 A1 | 11/2007 | Rosenthal |
| 2007/0299309 A1 | 12/2007 | Seibel et al. |
| 2008/0004643 A1 | 1/2008 | To et al. |
| 2008/0004644 A1 | 1/2008 | To et al. |
| 2008/0004645 A1 | 1/2008 | To et al. |
| 2008/0004646 A1 | 1/2008 | To et al. |
| 2008/0015491 A1 | 1/2008 | Bei et al. |
| 2008/0027334 A1 | 1/2008 | Langston |
| 2008/0033396 A1 | 2/2008 | Danek et al. |
| 2008/0045986 A1 | 2/2008 | To et al. |
| 2008/0058629 A1 | 3/2008 | Seibel et al. |
| 2008/0065124 A1 | 3/2008 | Olson |
| 2008/0065125 A1 | 3/2008 | Olson |
| 2008/0065205 A1 | 3/2008 | Nguyen et al. |
| 2008/0103439 A1 | 5/2008 | Torrance et al. |
| 2008/0103446 A1 | 5/2008 | Torrance et al. |
| 2008/0103516 A1 | 5/2008 | Wulfman et al. |
| 2008/0147000 A1 | 6/2008 | Seibel et al. |
| 2008/0154293 A1 | 6/2008 | Taylor |
| 2008/0221388 A1 | 9/2008 | Seibel et al. |
| 2008/0243030 A1 | 10/2008 | Seibel et al. |
| 2008/0243031 A1 | 10/2008 | Seibel et al. |
| 2008/0262312 A1 | 10/2008 | Carroll et al. |
| 2009/0018565 A1 | 1/2009 | To et al. |
| 2009/0018566 A1 | 1/2009 | Escudero et al. |
| 2009/0018567 A1 | 1/2009 | Escudero et al. |
| 2009/0024085 A1 | 1/2009 | To et al. |
| 2009/0024191 A1 | 1/2009 | Seibel et al. |
| 2009/0028407 A1 | 1/2009 | Seibel et al. |
| 2009/0099641 A1 | 4/2009 | Wu et al. |
| 2009/0135280 A1 | 5/2009 | Johnston et al. |
| 2009/0137893 A1 | 5/2009 | Seibel et al. |
| 2009/0208143 A1 | 8/2009 | Yoon et al. |
| 2009/0216180 A1 | 8/2009 | Lee et al. |
| 2009/0221904 A1 | 9/2009 | Shealy et al. |
| 2009/0235396 A1 | 9/2009 | Wang et al. |
| 2009/0244485 A1 | 10/2009 | Walsh et al. |
| 2009/0316116 A1 | 12/2009 | Melville et al. |
| 2010/0125253 A1 | 5/2010 | Olson |
| 2010/0241147 A1 | 9/2010 | Maschke |
| 2010/0274270 A1 | 10/2010 | Patel et al. |
| 2010/0305452 A1 | 12/2010 | Black et al. |
| 2010/0324472 A1 | 12/2010 | Wulfman |
| 2011/0004107 A1 | 1/2011 | Rosenthal et al. |
| 2011/0021926 A1 | 1/2011 | Spencer et al. |
| 2011/0118660 A1 | 5/2011 | Torrance et al. |
| 2011/0263936 A1 | 10/2011 | He et al. |
| 2012/0046679 A1 | 2/2012 | Patel et al. |

FOREIGN PATENT DOCUMENTS

| | | |
|---|---|---|
| RU | 2185859 C2 | 7/2002 |
| RU | 2218191 C2 | 12/2003 |
| WO | WO 00/54659 A1 | 9/2000 |
| WO | WO 2006/133030 A2 | 12/2006 |
| WO | WO 2008/087613 A2 | 7/2008 |
| WO | WO2009/006335 A1 | 1/2009 |
| WO | WO 2009/094341 A2 | 7/2009 |

OTHER PUBLICATIONS

Han et al.; In situ Frog Retina Imaging Using Common-Path OCT with a Gold-Coated Bare Fiber Probe; CFM6; San Jose, California; CLEO, May 4, 2008; 2 pages.

Muller et al.; Time-gated infrared fourier-domain optical coherence tomography; CFM5; San Jose, California; CLEO May 4, 2008; 2 pages.

Wang et al.; Common-path endoscopic Fourier domain OCT with a reference Michelson interferometer; Proceedings of the SPIE; vol. 7566; pp. 75660L-75660L-7; Jan. 2010.

Simpson et. al; U.S. Appl. No. 13/433,049 entitled "Occlusion-Crossing Devices, Imaging, and Atherectomy Devices," filed Mar. 28, 2012.

Aziz et al.; Chronic total occlusions—a stiff challenge requiring a major breakthrough: is there light at the end of the tunnel?; Heart; vol. 91; suppl. III; pp. 42-48; Jun. 2005.

CATHETER SYSTEM AND METHOD FOR BORING THROUGH BLOCKED VASCULAR PASSAGES

CROSS REFERENCE TO RELATED APPLICATIONS

This application is a continuation of U.S. patent application Ser. No. 12/108,433, filed on Apr. 23, 2008, entitled "CATHETER SYSTEM AND METHOD FOR BORING THROUGH BLOCKED VASCULAR PASSAGES", which is incorporated herein by reference in its entirety.

INCORPORATION BY REFERENCE

All publications and patent applications mentioned in this specification are herein incorporated by reference to the same extent as if each individual publication or patent application was specifically and individually indicated to be incorporated by reference.

BACKGROUND

A number of vascular diseases, such as coronary artery disease and peripheral vascular disease, are caused by the build-up of fatty atherosclerotic deposits (plaque) in the arteries. These deposits limit blood flow to the tissues that are supplied by that particular artery. Risk factors for this type of disease include advanced age, diabetes, high blood pressure, obesity, history of smoking, and high cholesterol or triglycerides.

When these deposits build up in the arteries of the heart, the problem is called coronary artery disease (CAD). When these deposits build up in the arteries of a limb, such as a leg, the condition is called peripheral artery disease (PAD). Symptoms of CAD—angina, heart disease, and heart attacks, are well known. Symptoms of PAD can include pain on walking, and wounds that do not heal. If PAD is not treated, it can eventually produce critical limb ischemia (CLI), gangrene, and loss of limb. Roughly 30% of the population over the age of 70 suffers from PAD.

When the plaque builds up to the point where an artery is totally occluded, the obstruction is referred to as a Chronic Total Occlusion (CTO). CTOs can confound the treatment of CAD, because the sudden loss of heart muscle can lead to sudden death. A CTO that occludes the peripheral arteries for PAD patients is also extremely serious. PAD patients that suffer from a CTO often enter a downward spiral towards death. Often the CTO in a peripheral artery results in limb gangrene, which requires limb amputation to resolve. The limb amputation in turn causes other complications, and roughly half of all PAD patients die within two years of a limb amputation.

For both CAD and advanced PAD, prompt treatment of such blockages is thus essential. Here, less invasive angioplasty or atherectomy procedures have many advantages. In these procedures, a catheter is inserted into the diseased artery and threaded to the blocked region. There the blockage may be either squeezed into a hopefully more open position by pressure from an inflated catheter balloon (balloon angioplasty), the blocked region may be kept open by a stent, or alternatively a physician may use a catheter to surgically remove the plaque from the inside of the artery (atherectomy).

As an example, for the treatment of PAD, atherectomy devices such as the Fox Hollow (now ev3) SilverHawk™ catheter (U.S. Pat. No. 6,027,514), are often used. These catheters may be threaded (usually with the aid of a guidewire) up the artery to a blocked region. There, the physician will usually position the catheter to make multiple passes through the blocked region of the artery, each time shaving a way a ribbon of plaque. The shaved ribbons of plaque are stored in the hollow nose of the device. By making multiple passes, the plaque may be substantially reduced, blood circulation may be restored to the limb, and the limb in turn saved from amputation.

In order to effectively treat the plaque, however, most modern catheters need to be threaded past the blocked region of the artery. This is because the active portions of most catheters, which are used to treat the blockage, are usually located on the side of the catheter, rather than on the tip of the catheter. This is due to simple mechanical necessity. The tip of the catheter must have a very small surface area, and thus is able to treat only a very small portion of the diseased artery. By contrast, the side of the catheter has a much larger surface area, and the catheter side thus conforms nicely to the sides of the diseased artery. Thus stents, balloons, atherectomy cutting tools, etc., are usually mounted on the sides of the catheter. The catheter must be threaded past the blocked portion of the artery in order to function properly.

When the artery is only partially blocked by plaque, the catheter can usually be maneuvered past the obstruction, and the active portions of the catheter can thus be brought into contact with the diseased portion of the artery. However when the artery is totally blocked, as is the case with a CTO, this option is no longer possible. The tip of the catheter encounters the obstruction, and further forward motion is blocked.

Simply trying to force a typical catheter past the obstruction usually isn't possible. The obstructions are typically composed of relatively tough fibrous material, which often also includes hard calcium deposits as well. Often, when physicians attempt to force guidewires or catheters past such obstructions, the guidewire or catheter device may instead exit the artery and enter the lumen outside the artery. This further damages the artery, further complicates the procedure, and decreases the chance of success. As previously discussed, the consequences of such procedure failures have a high mortality rate. Thus improved methods to allow catheters and guidewires to more readily penetrate through hardened plaque and CTO are thus of high medical importance.

A good summary of the present state of the art may be found in an article by Aziz and Ramsdale, "Chronic total occlusions—a stiff challenge requiring a major breakthrough: is there light at the end of the tunnel?" Heart 2005; 91; 42-48.

Previous attempts to produce devices for cutting through hardened plaque include U.S. Pat. Nos. 5,556,405 to Lary, 6,152,938 to Curry, and 6,730,063 to Delaney et. al.

U.S. Pat. No. 5,556,405 teaches an incisor catheter which features a bladed head stored in a catheter housing, which contains a number of slits though which the blades protrude. The blade is activated by a push-pull catheter. When the push-pull catheter is pushed, the bladed head protrudes through the slits in the housing, and the blade thus comes into contact with hardened plaque material. The blade does not rotate, but rather delivers linear cuts.

U.S. Pat. No. 6,152,938 teaches a general purpose catheter drilling device for opening a wide variety of different blocked (occluded) tubes. The device anchors the tip of the drill head against a face of the occlusion, and partially rotates the drill head using a rein attached to the drill head so that the drill head faces at an angle.

U.S. Pat. No. 6,730,063 teaches a catheter device for chemically treating calcified vascular occlusions. The device is a fluid delivery catheter that delivers acidic solutions and other fluids to calcified plaque with the objective of chemically dissolving the calcified material.

Several catheter devices for traversing CTO obstructions are presently marketed by Cordis Corporation, FlowCardia Technology, Kensey Nash Corporation, and other companies. Cordis Corporation, a Johnson and Johnson Company, produces the Frontrunner® XP CTO catheter (formerly produced by LuMend Corporation). This catheter, discussed in U.S. Pat. No. 6,800,085 and other patents, has a front "jaw" that opens and closes as it traverses the catheter. The jaw itself does not cut, but rather attempts to pry open the CTO as the catheter passes.

Other catheter devices use various forms of directed energy to traverse CTOs. For example, FlowCardia Technology, Sunnyvale Calif., produces the Crosser system, taught in U.S. Pat. No. 7,297,131 and other patents. This system uses an ultrasonic transducer to deliver energy to a non-cutting catheter head. This catheter head itself has a relatively small diameter and does not have any blades. Rather, the head, through rapid (ultrasonic) vibration is able to push its way through a variety of different occlusions.

Kensey Nash Corporation, Exton Pa. (formerly Intraluminal Therapeutics, Inc.), produces the Safe-Cross CTO system. This system, taught in U.S. Pat. Nos. 6,852,109 and 7,288,087, uses radiofrequency (RF) energy. The catheter itself is also directed in its movement by an optical (near-infrared light) sensor which can sense when the tip of the catheter is near the wall of the artery. The optical sensor tells the operator how to steer the catheter, and the RF ablation unit helps the operator ablate material and cross occluded regions.

Although ingenious, the success rates with these devices still leave much to be desired. According to Aziz, the best reported success rates of overcoming CTOs with prior art devices range from 56% to 75%. Aziz further teaches that the average success rates are only in the 50-60% range. Given the huge negative impact that unsuccessfully cleared CTO's have on patient morbidity and mortality, clearly further improvement is desirable. An additional problem with these prior art CTO clearing devices is that simply cutting a small channel though the CTO may not be sufficient to totally resolve the medical problem. Occasionally, the device that traverses the CTO should also remove (debulk) a substantial portion of the occlusion. This is because as previously discussed, removal of a substantial portion of the occlusion may be required in order to allow catheters with side mounted stents, balloons, and atherectomy cutting tools to get access to the damaged portions of the artery and make more lasting repairs. Thus improved CTO "unclogging" devices that can do the more substantial amount of CTO debulking required to allow other types of catheters to pass are also desirable.

Thus there remains a need for devices that can effectively traverse CTOs and remove more substantial amounts of hardened or calcified plaque. Such devices would enable stents and other devices, such as SilverHawk atherectomy catheters, balloon catheters, etc. to be more successfully used in high occlusion situations. This in turn should lead to improved patient outcomes and a reduction in patient morbidity and mortality.

SUMMARY OF THE DISCLOSURE

The present invention teaches a novel rotating cutting head catheter for creating a passage through refractory material, such as chronic total occlusions, refractory atherosclerotic plaque, gallstones, kidney stones, etc. from diseased arteries, veins, or other body lumens. The catheter's rotating cutting head is designed to reside safely within an outer protective sheath head when not in use, and this sheath head is mounted on the distal end of the catheter.

The outer protective sheath head contains one or more helical grooves or slots, and the cutting head contains protruding blades or projections that fit into these helical grooves or slots. Application of torque to an inner torque communicating connector (a catheter or wire or coil, or any torque communicating mechanism attached to the cutting head) applies spin to the cutting head, and the force of the sheath head's helical grooves against the cutting head's protruding blades or projections advances the cutting head outward from the protective sheath. Once extended, the cutting head may now rotate freely. In some embodiments, the center of the catheter and even the cutting head itself may be hollow, and the device may use a guidewire to direct the catheter and the cutting head to the desired position. Alternatively the guidewire may be attached to a guide that is attached to the outside of the catheter tube. In at least some embodiments, this sheath head acts as motion stop, and may contain one or more motion stop elements (such as a mechanical barrier) designed to restrict the forward extension of the cutting head.

Depending upon the angle and nature of the cutting head's protruding blades, the blades may either be designed to simply cut thorough the occluding material, without actually dislodging the occluding material from the body lumen, or alternatively the blades may be designed to both cut through the occluding material, and sever its link to the body lumen, thereby dislodging the occluding material from the body lumen. In this case, the cutting head can act to actually remove (debulk) a substantial portion of the occlusion.

DETAILED DESCRIPTION

Figure 1:
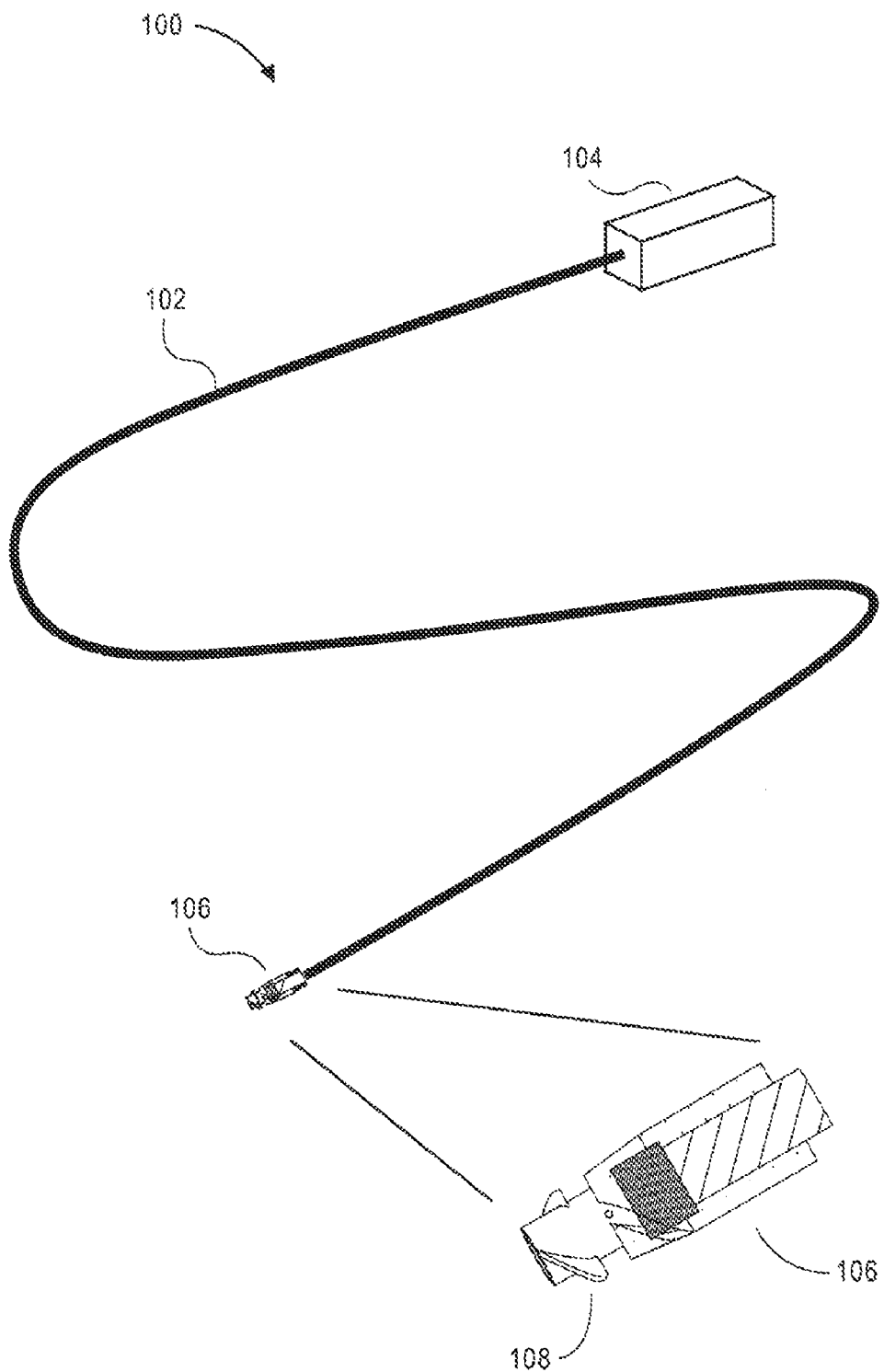
FIG. 1 shows an overview of the catheter device including the handle, the catheter, and the catheter head.

Although, throughout this discussion, applications of this device for creating a passage through refractory atherosclerotic plaque from arteries, particularly coronary or peripheral limb arteries, are frequently used as examples, it should be understood that these particular examples are not intended to be limiting. Other applications for the present technology may include removal of kidney stones, in which case the device will be intended to traverse the ureters; gallstones, in which case the device will be intended to traverse the bile duct; enlarged prostate blockage of the urethra, in which case the device will be intended to traverse the urethra; blocked fallopian tubes, in which case the device will be intended to traverse the fallopian tubes; treatment of blood clots, removal of material trapped in the lungs, etc. In general, any unwanted material occupying space in a body lumen may be surgically removed by these techniques. Similarly, although use in human patients is cited in most examples, it should be evident that the same techniques may be useful in animals as well.

Helical drill bits and self-tapping screw bits are widely known to be highly effective at penetrating through materials as soft as wax and as refractory as rock and metal, and indeed such devices are widely used for such purposes. Although effective, drill bits are typically considered to be both powerful and extremely crude. As anyone who has ever attempted to use an electric drill can attest, drill devices, although admittedly effective at removing material, would seem to be totally unsuited for delicate vascular surgery, particularly at sites hidden deep within the body. Helical self-tapping screw bits are designed slightly differently. Although just as effective at cutting through various materials, drill bits are configured to both cut and then remove the material, while self-tapping screw bits are designed primarily for cutting a passage through the material. For either type of device, the problem is not the efficacy of cutting or occlusion removal; the problem is one of preventing inadvertent damage to the surrounding artery.

Surprisingly however, the present invention teaches that if the prejudice against such crude and powerful methods is overcome, and suitable protection and control devices are devised to control the crude and apparently overwhelming power of such "drill bit" devices, catheter "drill bit" devices suitable for delicate vascular surgery, which are both powerful at cutting or removing occlusions, yet specific enough to avoid unwanted damage to artery walls, may be produced.

Thus, in a first aspect of the present invention, the superior material cutting/removing properties of a "drill bit" like material removal device (or self-threading helical screw bit) are combined with suitable protection and catheter guidance mechanisms which allow such powerful cutting devices to be safely and effectively used within the confines of delicate arteries and other body lumens.

To do this, precise control must be exerted over the cutting edge of the "drill bit". The bit or "cutting head" should normally be sheathed or shielded from contact with artery walls, so that inadvertent damage to artery walls can be avoided while the head of the catheter is being threaded to the artery to the occluded region. Once at the occlusion, the cutting portion of the cutting head (bit) should be selectively exposed only to the minimal extent needed to perform the relevant occlusion cutting activity. The rotation direction of the cutting head may optionally be varied, for example by rotating the head counter-clockwise to produce a blunt dissection through the obstacle or occlusion, and then clockwise while pulling back on the entire assembly. Once the desired cuts are made, the cutting head should then be quickly returned to its protective sheath. The entire device should operate within the millimeter diameters of a typical artery, and should be capable of being threaded on a catheter for a considerable distance into the body.

Suitable techniques to achieve these objectives are taught in the following figures and examples.

FIG. 1 shows an overview of the catheter device (100) including the catheter body (102), the catheter handle (104), and the catheter head (106). The catheter body and catheter head, and often even the cutting head, are often hollow and are capable of accommodating a guidewire (not shown). A magnified view of the catheter head, showing the rotating cutting head in an extended configuration (108), extended outside of the sheath portion of the catheter head (here this sheath is called the "sheath head") (106) is also shown.

Figure 2:
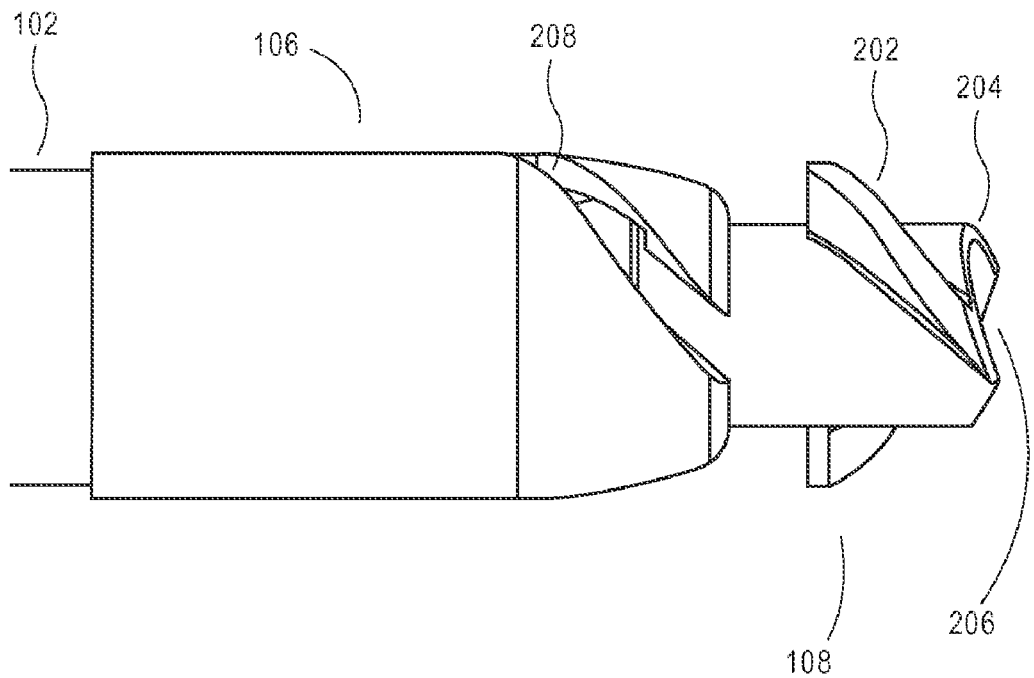
FIG. 2 shows the exterior of the catheter head with the cutting head extended out from the sheath head.

FIG. 2 shows the exterior of the sheath head portion of the catheter head (106) with the cutting head (108) extended. This cutting head will normally have one or more projecting side blades or with cutting edges (202), and additionally will often have cutting edges on the front (204) as well. The center of sheath head portion of the catheter head (106) and catheter (102) may be hollow to accommodate a guidewire. In some embodiments, the guidewire will exit the sheath portion of the catheter head (106) on the side of catheter head (106) prior to cutting head (108) by a side opening (not shown). In other embodiments, cutting head (108) will itself be hollow and the guidewire will exit the end of cutting head (108) through opening (206).

In the closed configuration, the rotating cutting head (108) is retracted inside the sheath head portion of catheter head (106) and the cutting edges or projections (202) from the cutting head (108) fit into helical slots or grooves (208). This sheathed configuration prevents projecting side cutting edges (202) and front cutting edges (204) from accidentally contacting the walls of the artery.

Figure 3:
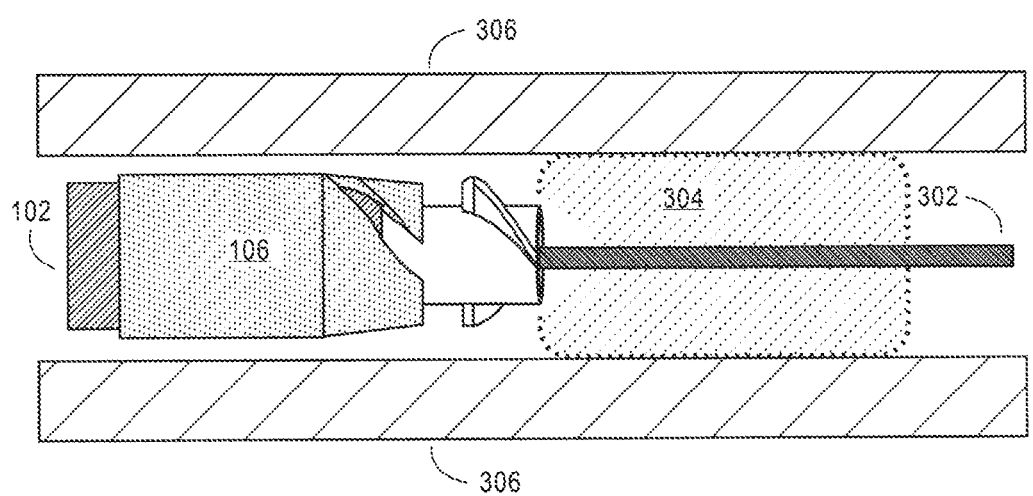
FIG. 3 shows a drawing of the catheter head (mounted on a guidewire) with the cutting head extended and cutting into a CTO plaque in an occluded artery.

FIG. 3 shows a drawing of the catheter head (106) (with the cutting head extended from the sheath head) cutting into a CTO (304) in an occluded artery (306). In this example, the catheter and catheter head are mounted on and guided by a guidewire (302), however this will not always be the case.

As should be clear, the cutting edge of the "drill bit/screw-thread" like cutting head can easily damage artery lining (306). In order to avoid such accidental damage, precise control over the extent of cutting head exposure is needed. Methods to achieve such precise control are shown in FIG. 4.

Figure 4:
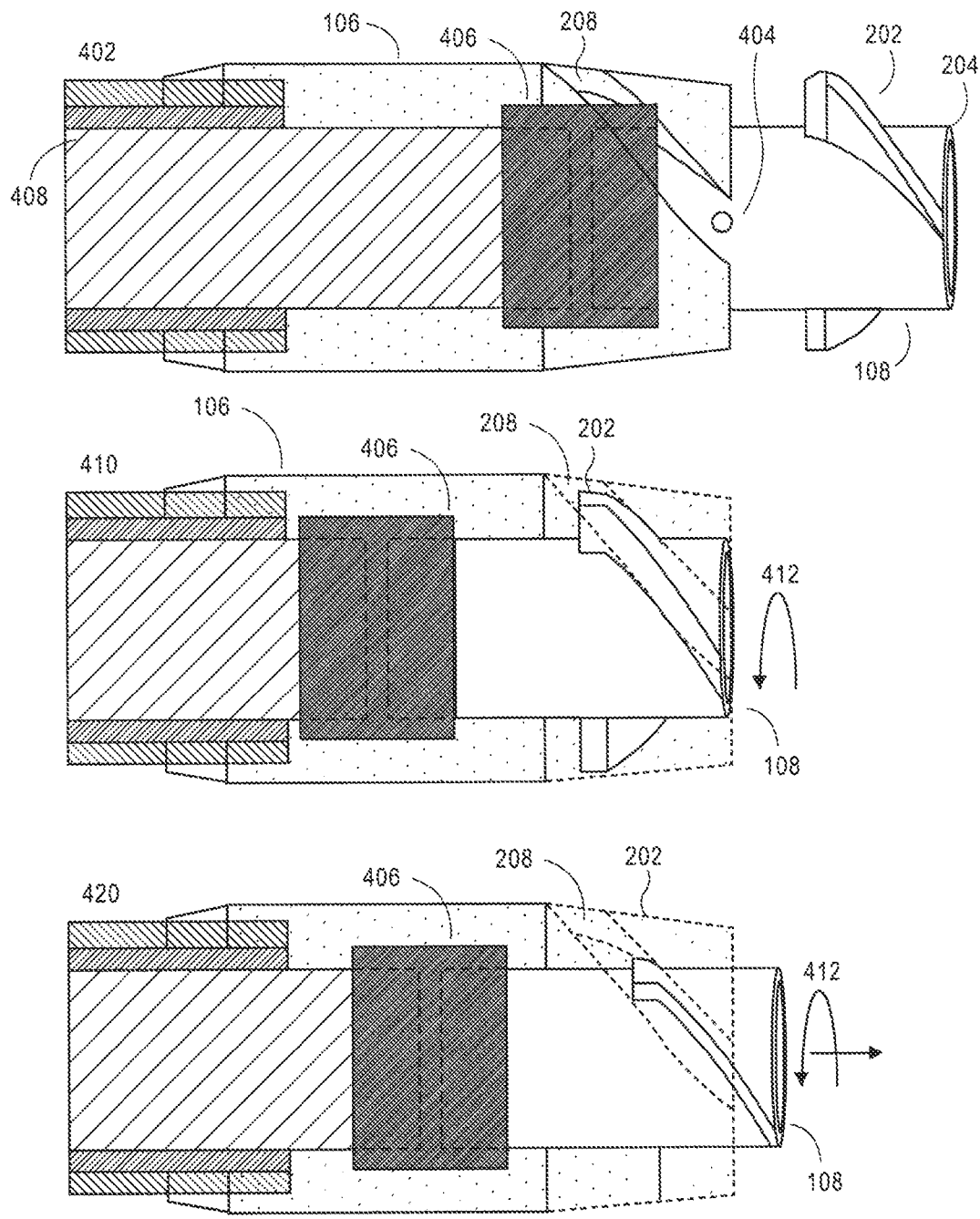
FIG. 4 shows a diagram of the cutting head unscrewing from protective shroud of the catheter head's sheath head.

FIG. 4 shows some of the details of how the cutting head (108) is unscrewed from the helical slots or grooves (208) of the sheath head portion of catheter head (106), thus exposing cutting edges (202) and (204). In (402), the cutting head (108) is shown fully exposed. The cutting head has become fully unscrewed from helical slots (208) and is fully extended. An optional projecting post or guide (404) mounted on cutting head (108) may act to guide the rotating cutting head into and out of the helical screw-like slots (208). The coupling (406) that couples cutting head (108) with a torque transmitting (torque communicating connector) inner catheter tube or cable (408) is in the extreme distal position inside of the sheath head portion of catheter head (106).

In (410), the cutting head is shown in its fully retracted position. Normally the cutting head will be stored in this fully retracted position so that it can be introduced into the artery via a guidewire, and be directed to the occlusion or plaque region, without damaging non-target regions of the artery. Note that the coupling (406) is in the fully distal position in the sheath head portion of catheter head (106), and that the protruding cutting blades (202) of cutting head (108) are fully screwed into helical screw slots (208).

In some situations, a guidewire [FIG. 3 (302)] leading to the obstruction will already have been introduced. In fact, a previous attempt to perform atherectomy may have already been made, and this attempt may have been frustrated by refractory plaque, such as a plaque covered with hard calcium deposits, whereupon the physician may make a decision to use the present cutting device to punch through this refractory plaque.

In use, the catheter head (106) and catheter tube (102) are attached to the guidewire and are then introduced into the artery via an appropriate incision. The catheter handle (104) will remain outside of the body. The location of the obstruction will generally be known, and in fact the obstruction may be imaged by fluoroscopy or other technique. Catheter head (106) is brought up against the obstruction, and the operator will then apply torque, often via a device mounted on catheter handle (104). This torque is usually transmitted to the catheter head (106) via an inner torque conducting catheter or wire (408), here termed a "torque communicating connector". Usually outer catheter (102) will not conduct torque. Outer catheter (102) remains approximately stationary (i.e. does not rotate) and similarly the sheath head portion of catheter head (106) and the helical screw slots or grooves (208) also do not rotate.

The torque is communicated via coupling (406) to cutting head (108). This torque essentially causes cutting head (108) to "unscrew" from its retracted position in the sheath head portion of catheter head (106) via the action of the protruding blade edges (202) against helical slots or grooves (208). This "unscrewing" circular motion is shown by the curved arrow (412). As cutting head (108) unscrews, it starts to advance and protrude outside of the protective sheath head shroud.

In (420), the cutting head (108) is now shown in a partially unscrewed or partially extended position. Note that the protruding blade edges (202) have moved relative to the helical sheath head screw slots or grooves (208). Thus the blade edges (202) are now partially unscrewed from the helical screw slots (208) and are partially exposed. Cutting head (108) now is protruding out from the sheath head portion of catheter head casing or shroud (106), and the coupling (406) has moved partially toward the distal end of the catheter.

It should be evident that by reversing the direction of the torque, the cutting head may be again retracted into the sheath head when this is desired. The catheter can be repositioned for another cut, and the process of cutting head extension, cutting, and retraction can be repeated as many times as necessary.

Thus the present invention controls the aggressive cutting power of the "drill bit" cutting head by exposing only as much of the cutting head at a time as needed for the task at hand.

Figure 5:
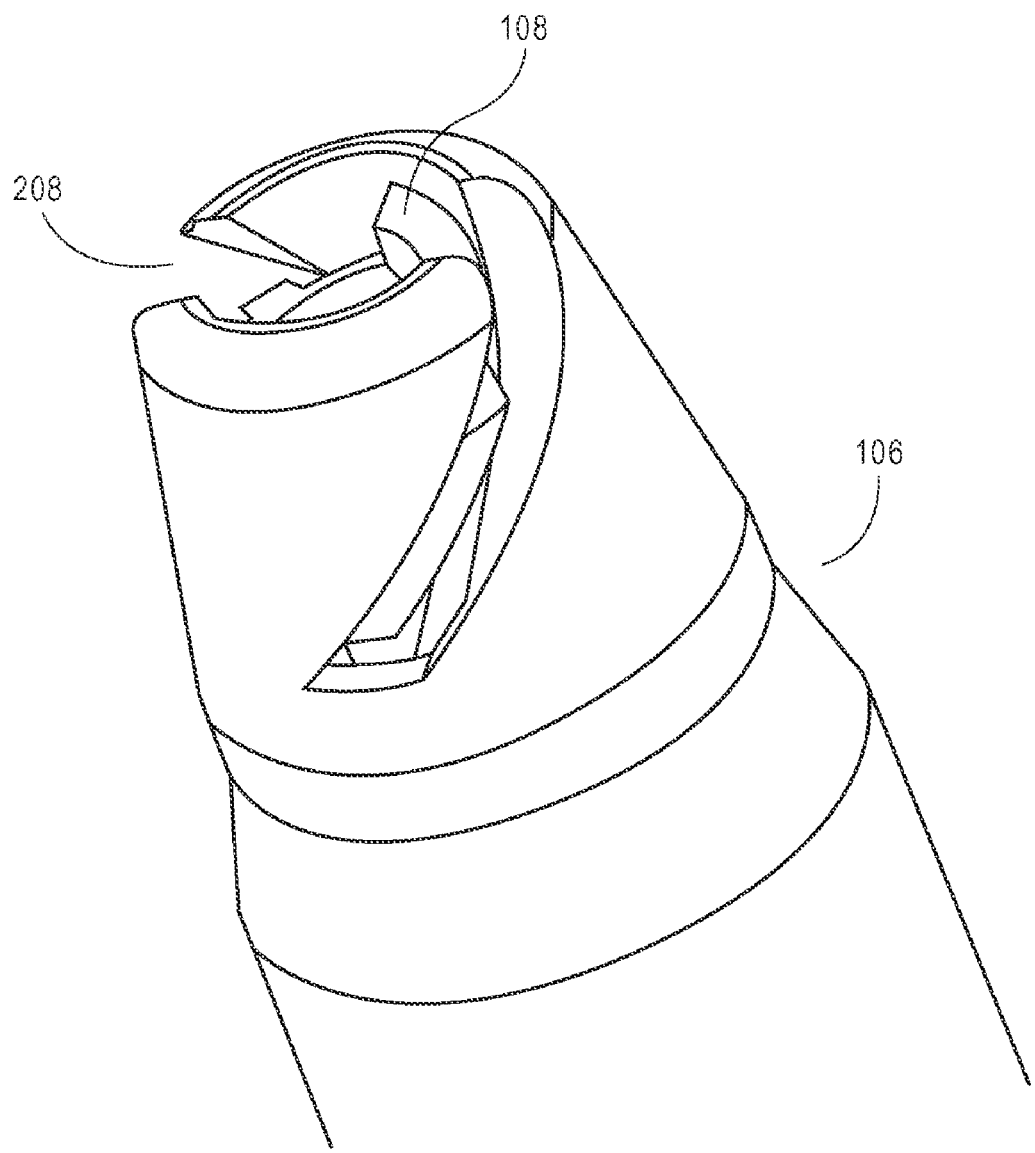
FIG. 5 shows a close up of the catheter head showing the cutting head screwed into a stored position inside the catheter head's protective sheath head.

FIG. 5 shows a close up of the sheath head portion of the catheter head showing the cutting head screwed into a stored position inside the protective sheath head shroud. This angle allows the helical screw slots or grooves (208) to be easily seen, and cutting head (108) can also be seen inside of the sheath head portion of catheter head (106).

Figure 6:
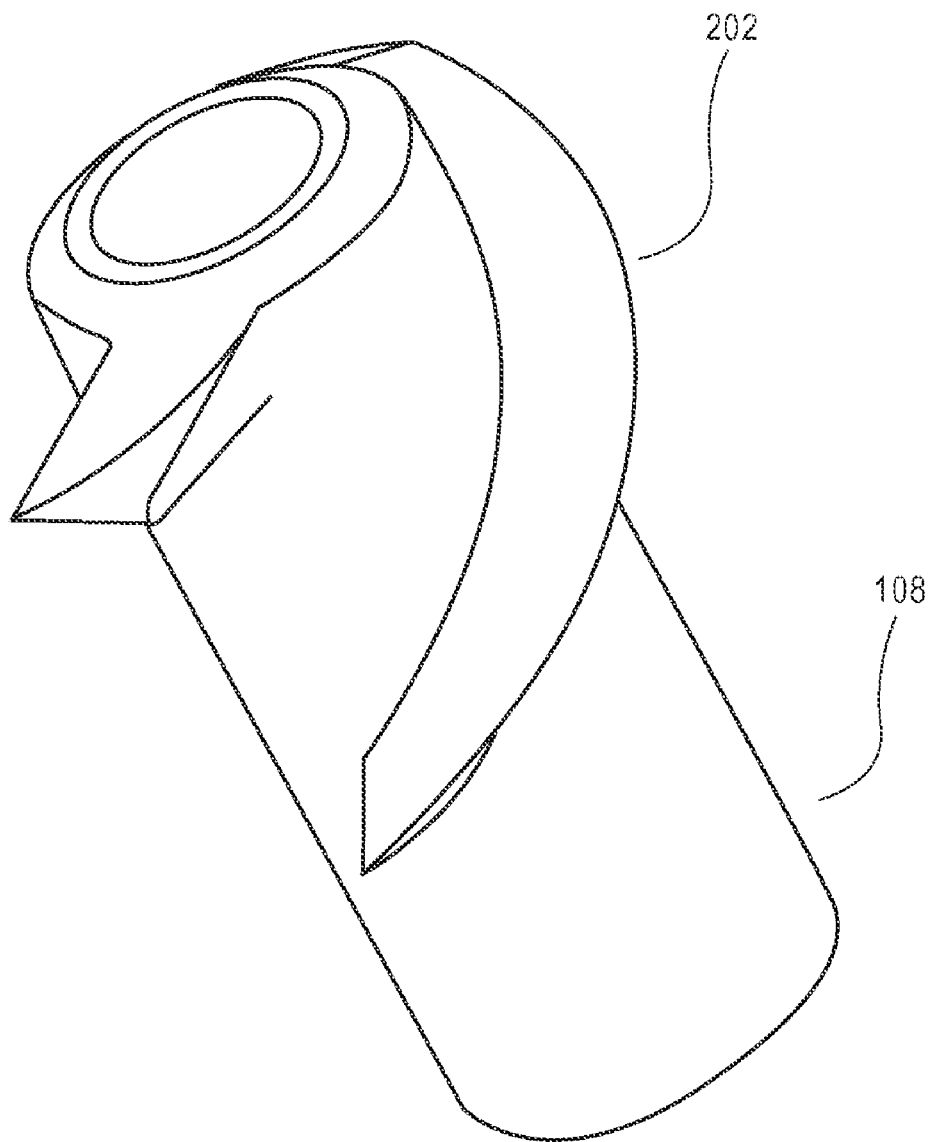
FIG. 6 shows a close up of a cutting head with an alternate protruding blade design.
Figure 1:
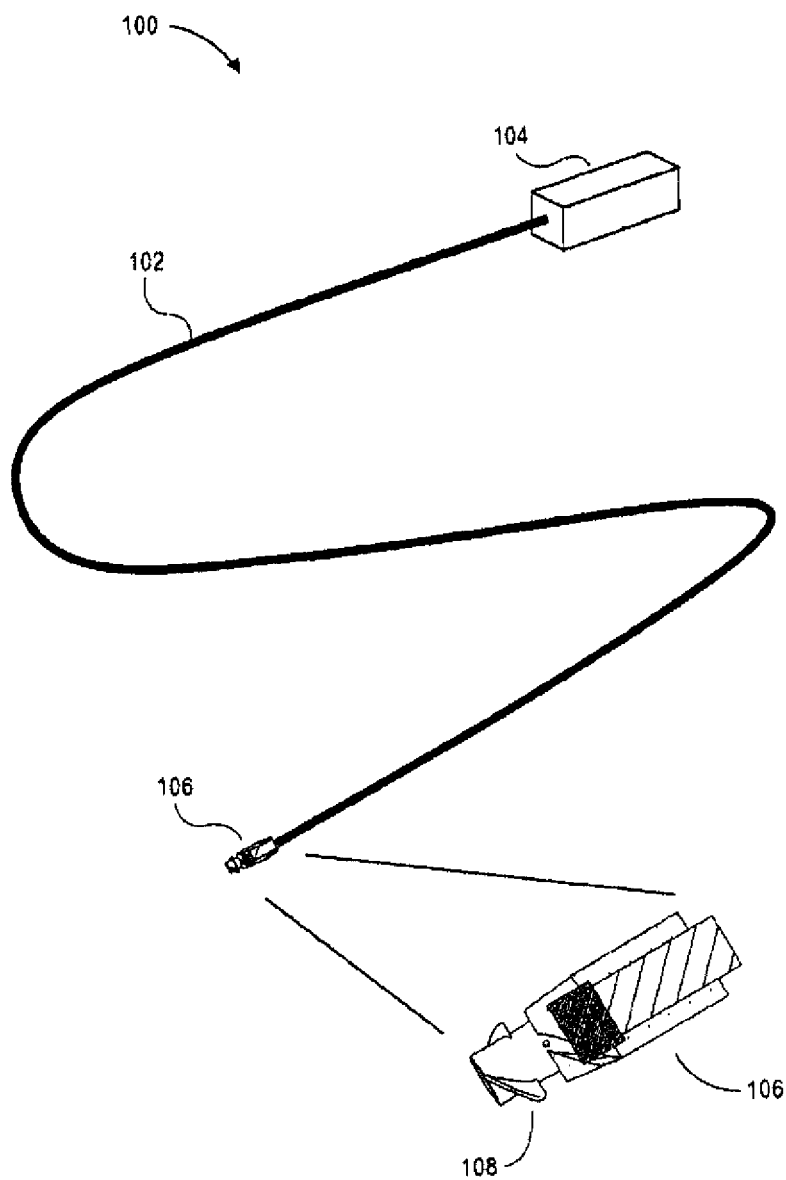
Figure 2:
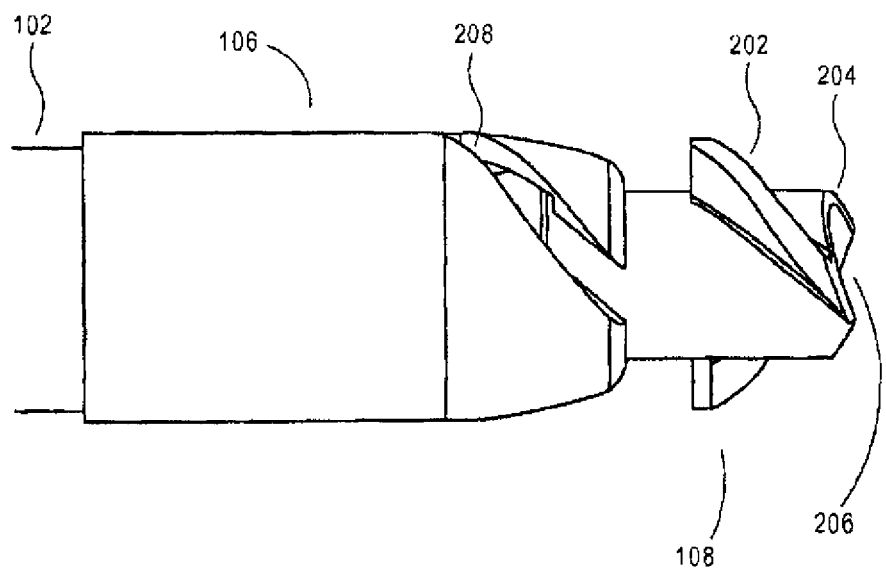
Figure 3:
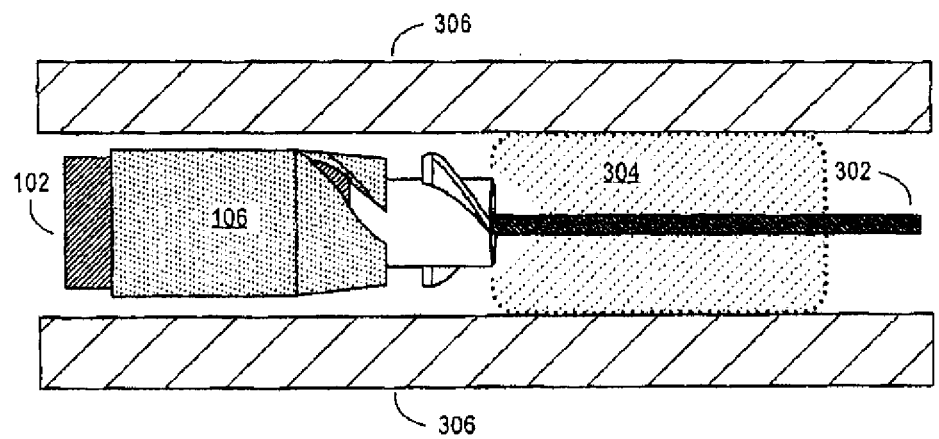
Figure 5:
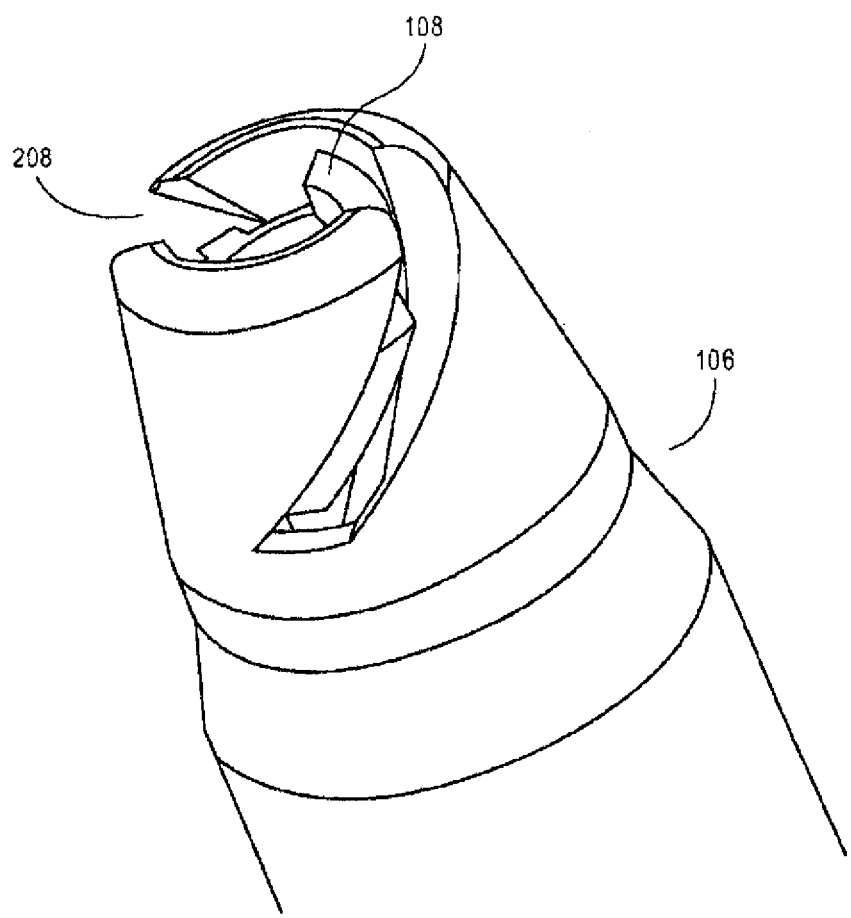
Figure 6:
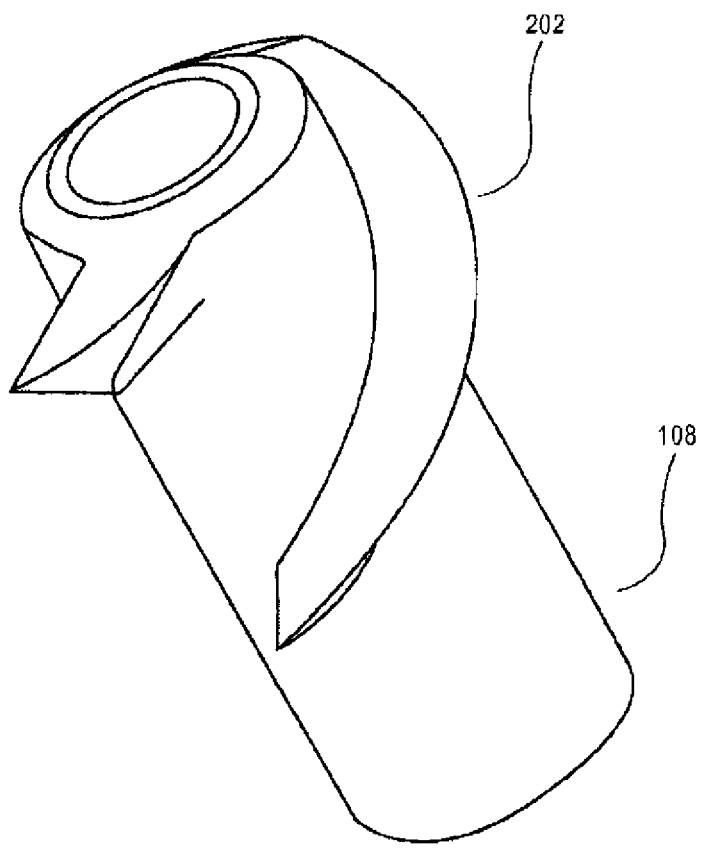

FIG. 6 shows a close up of an alternate design cutting head (108) with spiral shaped protruding cutting edges (202).

The sheath head portion of catheter head (106) will normally be between about 1 to 2.2 millimeters in diameter, and the catheter body (102) will typically also have a diameter of approximately 1 to 3 millimeters (3-9 French), and a length between 50 and 200 cm. The sheath head may be made from various materials such as hard plastics, metals, or composite materials. Examples of such materials include NiTi steel, platinum/iridium or stainless steel.

Although sheath head (106) contains slots or grooves designed to impart forward motion to cutting head (108) when cutting head is rotated, and although these slots or grooves are referred to as "helical" grooves or slots, due to the short length of the sheath head and overall catheter head, the slots or grooves do not have to be in the exact mathematical shape of a helix. In fact a variety of shapes that differ somewhat from a mathematically pure helix configuration will suffice. In general, the slot or groove must be such that torque applied to the cutting head causes the cutting head to both rotate and advance, and any such slot or groove is here designated as a "helical" slot or groove. Also, for this discussion, a "slot" is considered to be an opening that extends from the inside to the outside of the hollow catheter head (106), while a "groove" is similar to a rifle groove in that a "groove" does not extend all the way from the inside of the hollow sheath head to the outside, but rather only penetrates partway through the sheath head material.

The cutting head (108) will often be made of materials such as steel, carbide, or ceramic. The blades of the cutting head (202), (204) can optionally be hardened by coating with tungsten carbide, ME-92, etc. Materials suitable for this purpose are taught in U.S. Pat. Nos. 4,771,774; 5,312,425; and 5,674,232. The angle of the blades and the details of their design will differ depending upon if the head is intended to simply cut through the occluding material, of if it is intended to cut through and actually remove (debulk) portions of the occlusion. For example, blades intended for to remove material may curve at an angle such that they will tend to sever the link between the occluding material and the body lumen, while blades intended just for cutting will have an alternate angle that tends not to sever this link.

In some embodiments, the catheter may be composed of two different tubes. In this configuration, there may be an outer catheter tube (102), which will often be composed of a flexible biocompatible material. There may also be an inner tube (408) chosen for its ability to transmit torque from the catheter handle (104) to the cutting head (108) (via coupling (406)). The inner torque transmitting tube (which is one possible type of "torque communicating connector") is able to twist relative to the outer catheter tube so that when torque is applied to the inner tube at the handle end (104), the cutting head (108) will rotate, but the catheter sheath head itself, which is connected to the outer catheter tube, will remain roughly stationary. Alternatively a cable may be used in place of inner tube (408).

The outer catheter body (102) may often be made from organic polymer materials extruded for this purpose, such as polyester, polytetrafluoroethylene (PTFE), polyurethane, polyvinylchloride, silicon rubber, and the like. The inner torque conducting catheter (408) may be composed of these materials or alternatively may be composed from metal coils, wires, or filaments.

In many embodiments, the catheter will be designed to be compatible with a monorail guidewire that has a diameter of about 0.014", or between 0.010" and 0.032". For example, the outer catheter jacket may contain attached external guides for the monorail guidewire. In this case, the guidewire may exit these external guides either prior to the catheter head, or midway through the catheter head. Alternatively, the catheter may be hollow, and be located over the guidewire for the entire length of the catheter.

The catheter handle (104) will normally attach to both outer catheter tube (102), and inner tube or cable (408). Usually handle (104) will contain at least a knob, dial, or lever that allows the operator to apply torque to the inner torque transmitting tube or cable (408). In some embodiments, sensors may be used to determine how much the cutting head (108) has rotated or extended relative to the sheath head portion of catheter head (106), and these sensors, possibly aided by a mechanical or electronic computation and display mechanism, may show the operator how much the cutting head has rotated and or extended.

In some embodiments, the catheter handle (104) will be designed with knobs or levers coupled to mechanical mechanisms (such as gears, torque communicating bands, etc.) that manually rotate and advance/retract the catheter tip, and the operator will manually control the tip with gentle slow rotation or movement of these knobs or levers. In other embodiments the catheter handle will contain a mechanism, such as an electronic motor, and a control means, such as a button or trigger, that will allow the user to rotate and advance the cutting head in a precise and controlled manner. This mechanism may, for example, consist of a microprocessor or feedback controlled motor, microprocessor, and software that may act to receive information from a cutting head rotation or extension sensor, and use this rotation feedback data, in conjunction with operator instructions delivered by the button or trigger, to advance or retract the cutting head by a precise amount for each operator command. This way the operator need not worry about any errors induced by the spring action of the inner torque transmitting tube or cable (408). The microprocessor (or other circuit) controlled motor can automatically compensate for these errors, translate button or trigger presses into the correct amount of torque, and implement the command without requiring further operator effort. Alternatively non-microprocessor methods, such as a vernier or a series of guided markings, etc., may be used to allow the operator to compensate for differences in the rotation of the torque communicating connector and the rotation of the cutting head, or for the extent that which said cutting head exits said hollow sheath head.

In some embodiments, the catheter head may be equipped with additional sensors, such as ultrasonic sensors to detect calcified material, optical (near infrared) sensors to detect occlusions or artery walls, or other medically relevant sensors. If these sensors are employed, in some cases it may be convenient to locate the driving mechanisms for these sensors in the catheter handle (104) as well.

Additional means to improve the efficacy of the cutting head may also be employed. Thus the cutting head may be configured to vibrate at high (ultrasonic) frequency, perform radiofrequency (RF) tissue ablation, generate localized areas of intense heat, conduct cutting light (e.g. laser or excimer laser), or other directed energy means.

The cutting head may be composed of alternative designs and materials, and these designs and materials may be selected to pick the particular problem at hand. As an example, a cutting head appropriate for use against a calcified obstruction may differ from the cutting head appropriate for use against a non-calcified obstruction. Similarly the cutting head appropriate for use against a highly fibrous obstruction may be less appropriate against a less fibrous and fattier obstruction. The length or size of the obstruction may also influence head design.

Although multiple catheters, each composed of a different type of cutting head, may be one way to handle this type of problem, in other cases, a kit composed of a single catheter and multiple cutting heads (108) and optionally multiple sheath heads (106) may be more cost effective. In this type of situation, the cutting heads (108) may be designed to be easily mounted and dismounted from coupling (406). A physician could view the obstruction by fluoroscopy or other technique, and chose to mount the cutting head design (and associated sheath head design) best suited for the problem at hand. Alternatively, if the blades (202), (204) on cutting head (108) have become dull or chipped from use during a procedure, a physician may chose to replace dull or chipped cutting head (108) with a fresh cutting head, while continuing to use the rest of the catheter.

For some applications, it may also be useful to supply various visualization dyes or therapeutic agents to the obstruction using the catheter. Here, the dye or therapeutic agent may be applied by either sending this dye up to the catheter head through the space between the exterior catheter (102) and the interior torque catheter (408), or alternatively if torque catheter (408) is hollow, through the interior of torque catheter (408). If cutting head (108) also has a hollow opening (206), then the dye or therapeutic agent may be applied directly to time obstruction, even while cutting head (108) is cutting through the obstruction.

Examples of useful dyes and therapeutic agents to apply include fluoroscopic, ultrasonic, MRI, fluorescent, or luminescent tracking and visualization dyes, anticoagulants (e.g. heparin, low molecular weight heparin), thrombin inhibitors, anti-platelet agents (e.g. cyclooxygenase inhibitors, ADP receptor inhibitors, phosphodiesterase inhibitors, Glycoprotein inhibitors, adenosine reuptake inhibitors), anti-thromboplastin agents, anti-clot agents such as thrombolytics (e.g. tissue plasminogen activator, urokinase, streptokinase), lipases, monoclonal antibodies, and the like.

In some embodiments, it may be useful to construct the cutting head out of a material that has a radiopaque signature (different appearance under X-rays) that differs from the material used to construct the hollow sheath head portion of the catheter head. This will allow the physician to directly visualize, by fluoroscopic or other x-ray imaging technique, exactly how far the cutting head has advanced outside of the catheter sheath head.

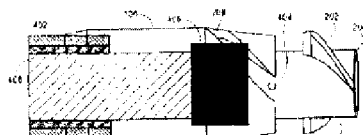

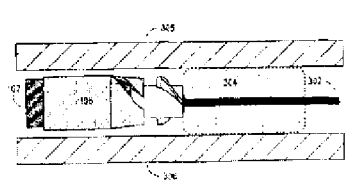

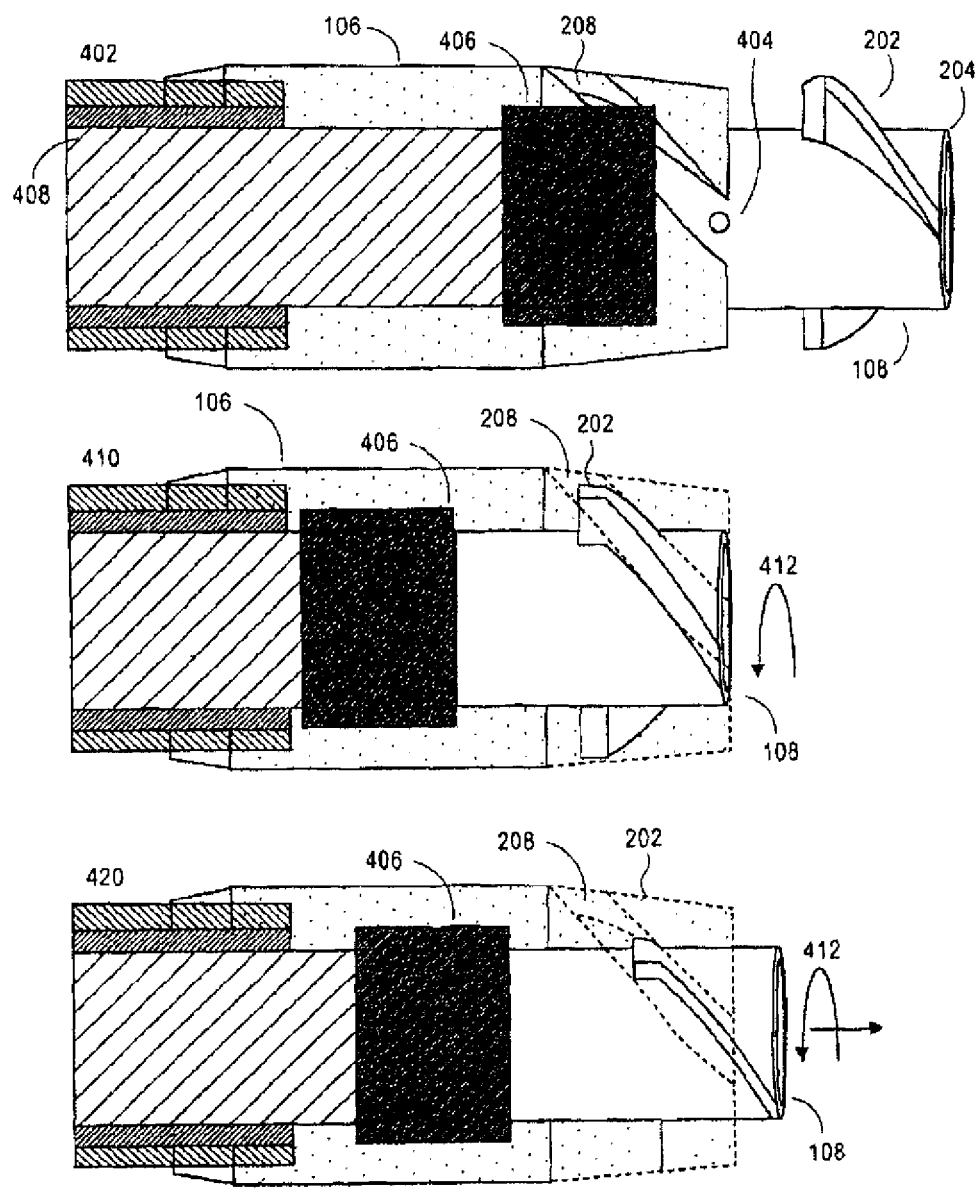

What is claimed is:

1. A method of delivering a guidewire across an atherosclerotic occlusion or lesion in a vascular lumen while protecting the vascular lumen, said method comprising:
    passing a distal end of a catheter tube having a rotatable cutting head and a sheath through the vascular lumen to the occlusion or lesion, wherein the rotatable cutting head is retracted within the sheath during the passing step such that one or more helical cutting surfaces extending proximally along the rotatable cutting head are engaged with one or more helical slots extending laterally through a sidewall of the sheath;
    extending the rotatable cutting head from the sheath such that the one or more helical cutting surfaces extend at least partially out of the sheath;
    rotating the rotatable cutting head;
    advancing said rotating cutting head across said occlusion or lesion to pass through occluding material without removing the occluding material; and
    passing a guidewire through a guidewire passageway extending through the catheter tube after the distal end of the catheter tube has passed beyond the atherosclerotic occlusion so that the guidewire spans the atherosclerotic occlusion or lesion.

2. The method of claim 1, wherein the rotatable cutting head is rotated by rotation of a drive shaft extending the length of the catheter.

3. The method of claim 1, further comprising varying the direction of rotation of the rotatable cutting head as it is advanced across the occlusion or lesion.

4. The method of claim 1, further comprising alternately rotating the rotatable cutting head clockwise and counterclockwise as the rotating cutting head is advanced across the occlusion or lesion.

5. The method of claim 1, further comprising dispensing a therapeutic agent or visualization dye agent through the catheter tube.

6. The method of claim 1, wherein the advancing step comprises cutting the occlusion or lesion with the one or more helical cutting surfaces on said rotatable cutting head.

7. The method of claim 1, further comprising applying ultrasonic vibration, radiofrequency (RF) energy, or light energy to the cutting head, occlusion, or lesion.

8. The method of claim 1, further comprising using the guidewire spanning the atherosclerotic occlusion or lesion to treat the occlusion or lesion by atherectomy, stenting, or balloon angioplasty during the same procedure.

9. The method of claim 1, further comprising imaging the vascular lumen as the rotatable cutting head is advanced.

10. A method of delivering a guidewire across an atherosclerotic occlusion or lesion in a vascular lumen while protecting the vascular lumen, said method comprising:

passing a distal end of a catheter tube having a rotatable cutting head and a sheath through the vascular lumen to the occlusion or lesion, wherein the rotatable cutting head is retracted within the sheath during the passing step such that one or more helical cutting surfaces extending proximally along the rotatable cutting head are engaged with one or more helical slots extending laterally through a sidewall of the sheath;

extending the rotatable cutting head from the sheath such that the one or more helical cutting surfaces extend at least partially out of the sheath;

rotating the rotatable cutting head alternately clockwise and counterclockwise;

advancing said rotating cutting head across said occlusion or lesion to pass through occluding material without removing the occluding material;

imaging the vascular lumen as the rotatable cutting head is advanced; and passing a guidewire through a guidewire passageway extending through the catheter tube after the distal end of the catheter tube has passed beyond the atherosclerotic occlusion so that the guidewire spans the atherosclerotic occlusion or lesion.

11. A method of delivering a guidewire across an atherosclerotic occlusion or lesion in a vascular lumen while protecting the vascular lumen, said method comprising:

passing a distal end of a catheter tube having a rotatable cutting head and a sheath through the vascular lumen to the occlusion or lesion, wherein the rotatable cutting head is retracted within the sheath during the passing step such that one or more helical cutting surfaces extending proximally along the rotatable cutting head are engaged with one or more helical slots extending laterally through a sidewall of the sheath to shield the one or more helical cutting surfaces from contact with the vascular lumen;

extending the rotatable cutting head from the sheath such that the one or more helical cutting surfaces extend at least partially out of the sheath;

rotating the rotatable cutting head;

advancing said rotating cutting head across said occlusion or lesion to pass through occluding material without removing the occluding material; and passing a guidewire through a guidewire passageway extending through the catheter tube after the distal end of the catheter tube has passed beyond the atherosclerotic occlusion so that the guidewire spans the atherosclerotic occlusion or lesion.

12. The method of claim 11, wherein the rotatable cutting head is rotate by rotation of a drive shaft extending the length of the catheter.

13. The method of claim 11, further comprising varying the direction of rotation of the rotatable cutting head as it is advanced across the occlusion or lesion.

14. The method of claim 11, further comprising dispensing a therapeutic agent or visualization dye agent through the catheter tube.

15. The method of claim 11, further comprising applying ultrasonic vibration, radiofrequency (RF) energy, or light energy to the cutting head, occlusion, or lesion.

16. The method of claim 11, further comprising using the guidewire spanning the atherosclerotic occlusion or lesion to treat the occlusion or lesion by atherectomy, stenting, or balloon angioplasty during the same procedure.

17. The method of claim 11, further comprising imaging the vascular lumen as the rotatable cutting head is advanced.

* * * * *

UNITED STATES PATENT AND TRADEMARK OFFICE
CERTIFICATE OF CORRECTION

PATENT NO. : 8,361,097 B2  
APPLICATION NO. : 13/277167  
DATED : January 29, 2013  
INVENTOR(S) : Himanshu N. Patel Page 1 of 8

It is certified that error appears in the above-identified patent and that said Letters Patent is hereby corrected as shown below:

Delete Title Page, Illustrating Figs. 3-4, and replace with new Title Page. (Attached)

In the Drawings

Delete Drawing Sheets 1-6 and substitute therefore the attached Drawing Sheets 1-6.

In the Specification

Column 10, line 6-7; After "Glycoprotein", insert --IIB/IIIA--.

In the Claims

Claim 12, column 12, line 18; after "head is" and before "by rotation", delete "rotate" and insert --rotated--.

Signed and Sealed this  
Seventeenth Day of June, 2014

Michelle K. Lee  
*Deputy Director of the United States Patent and Trademark Office*

(12) United States Patent
Patel et al.

(10) Patent No.: US 8,361,097 B2
(45) Date of Patent: Jan. 29, 2013

(54) CATHETER SYSTEM AND METHOD FOR BORING THROUGH BLOCKED VASCULAR PASSAGES

(75) Inventors: Himanshu N. Patel, San Jose, CA (US); John B. Simpson, Woodside, CA (US)

(73) Assignee: Avinger, Inc., Redwood City, CA (US)

(*) Notice: Subject to any disclaimer, the term of this patent is extended or adjusted under 35 U.S.C. 154(b) by 0 days.

(21) Appl. No.: 13/277,167

(22) Filed: Oct. 19, 2011

(65) Prior Publication Data
US 2012/0041307 A1 Feb. 16, 2012
US 2012/0209112 A2 Aug. 16, 2012

Related U.S. Application Data

(63) Continuation of application No. 12/108,433, filed on Apr. 23, 2008, now Pat. No. 8,062,316.

(51) Int. Cl.
*A61B 17/22* (2006.01)
*A61D 1/02* (2006.01)

(52) U.S. Cl. .......... 606/159; 606/171; 606/185; 606/80

(58) Field of Classification Search .......... 606/159, 606/194, 180, 80, 185, 171, 170; 30/29.5, 30/143, 151; 604/22, 164.01
See application file for complete search history.

(56) References Cited

U.S. PATENT DOCUMENTS

| | | |
|---|---|---|
| 4,178,935 A | 12/1979 | Gekhaman et al. |
| 4,552,554 A | 11/1985 | Gould et al. |
| 4,654,024 A | 3/1987 | Crittenden et al. |
| 4,686,982 A | 8/1987 | Nash |
| 4,771,774 A | 9/1988 | Simpson et al. |
| 5,047,040 A | 9/1991 | Simpson et al. |
| 5,085,662 A | 2/1992 | Willard |
| 5,182,291 A | 1/1993 | Gubin et al. |
| 5,190,050 A | 3/1993 | Nitzsche |
| 5,312,415 A | 5/1994 | Palermo |
| 5,312,425 A | 5/1994 | Evans et al. |
| 5,321,501 A | 6/1994 | Swanson et al. |
| 5,358,472 A | 10/1994 | Vance et al. |

(Continued)

FOREIGN PATENT DOCUMENTS

| | | |
|---|---|---|
| EP | 1859732 A1 | 11/2007 |
| KR | 2007/0047221 | 5/2007 |

(Continued)

OTHER PUBLICATIONS

Sharma et al.; Optical coherence tomography based on an all-fiber autocorrelator using probe-end reflection as reference; CWJ13; San Francisco, California; CLEO May 16, 2004; 4 pages.

(Continued)

*Primary Examiner* — Ryan Severson
*Assistant Examiner* — Tin Nguyen
(74) *Attorney, Agent, or Firm* — Shay Glenn LLP

(57) ABSTRACT

A rotating cutting head catheter for passage through chronic total occlusions or other refractory atherosclerotic plaque from diseased arteries is disclosed. The catheter's rotating cutting head is designed to reside safely within an outer protective sheath when not in use. The outer protective sheath contains one or more helical grooves or slots, and the cutting head contains protruding blades or projections that fit into these helical grooves or slots. Application of torque to an inner catheter or wire attached to the cutting head applies spin to the cutting head, and the force of the sheath's helical grooves or slots against the cutting head's protruding blades or projections advances the cutting head outward from the protective sheath. Once extended, the cutting head may now rotate freely. The device may use a guidewire to direct the cutting head to the desired position.

17 Claims, 6 Drawing Sheets